United States Patent
Jia

(10) Patent No.: US 11,464,667 B2
(45) Date of Patent: Oct. 11, 2022

(54) METHOD OF URINATION AND DEFECATION IN SPACE

(71) Applicant: Ansheng Jia, Xiangyang (CN)

(72) Inventor: Ansheng Jia, Xiangyang (CN)

( * ) Notice: Subject to any disclaimer, the term of this patent is extended or adjusted under 35 U.S.C. 154(b) by 53 days.

(21) Appl. No.: 16/575,398

(22) Filed: Sep. 19, 2019

(65) Prior Publication Data

US 2020/0146872 A1    May 14, 2020

(30) Foreign Application Priority Data

Nov. 9, 2018 (CN) .......................... 201811331134.6

(51) Int. Cl.
*A61F 5/44* (2006.01)
*A61M 1/00* (2006.01)
*B64G 1/60* (2006.01)
*B64G 6/00* (2006.01)

(52) U.S. Cl.
CPC .......... *A61F 5/4408* (2013.01); *A61F 5/4405* (2013.01); *A61M 1/0023* (2013.01); *B64G 1/60* (2013.01); *B64G 6/00* (2013.01)

(58) Field of Classification Search
CPC ...... A61F 5/4408; A61F 5/4405; A61F 5/442; A61F 5/453; A61F 5/455; A61F 5/451; A61M 1/00223; B64G 1/60; B64G 6/00; A41B 9/12; A61G 9/00
See application file for complete search history.

(56) References Cited

U.S. PATENT DOCUMENTS

| 2,749,558 | A | * | 6/1956 | Lent | ....................... B64D 11/02 |
| | | | | | 4/454 |
| 4,281,655 | A | | 8/1981 | Terauchi | |
| 5,334,174 | A | * | 8/1994 | Street | ..................... A61F 5/451 |
| | | | | | 604/315 |
| 2003/0181880 | A1 | * | 9/2003 | Schwartz | ............. A61G 5/1054 |
| | | | | | 604/358 |

(Continued)

FOREIGN PATENT DOCUMENTS

| CN | 101856288 A | 10/2010 |
| CN | 105664336 A | 6/2016 |

(Continued)

OTHER PUBLICATIONS

"KR 20100036663 Translation, 2008, Google patents, https://patents.google.com/patent/KR20100036663A/en?oq=KR+20100036663+A" (Year: 2008).*

(Continued)

*Primary Examiner* — Tatyana Zalukaeva
*Assistant Examiner* — Hans Kaliher
(74) *Attorney, Agent, or Firm* — Syncoda LLC; Feng Ma

(57) ABSTRACT

The disclosure belongs to the field of aerospace technology, and in particular relates to a method of urination and defecation in space. The method may include: forming a sealed space between a spacesuit below the waist and above the two thighs and the human skin before an astronaut urinates or defecates, and using, by the astronauts, the sealed space to urinate or defecate. The disclosure can confine the excrements in a small sealed space, and the operation thereof is simple, convenient and fast, and no excessive cost is required, and no pollution is caused in the spacesuit and the cabin, facilitating the astronauts' work in space.

6 Claims, 1 Drawing Sheet

(56) References Cited

U.S. PATENT DOCUMENTS

| | | | | |
|---|---|---|---|---|
| 2016/0106570 A1* | 4/2016 | Paley | ................ | A61F 13/49007 |
| | | | | 604/355 |
| 2018/0280189 A1* | 10/2018 | Kaufman | ................. | B64G 6/00 |
| 2021/0236345 A1* | 8/2021 | Glaug | ..................... | A61F 13/66 |

FOREIGN PATENT DOCUMENTS

| KR | 20100036663 A | * | 4/2010 |
|---|---|---|---|
| WO | 2007034774 A1 | | 3/2007 |

OTHER PUBLICATIONS

Office action of Russian patent office.

* cited by examiner

METHOD OF URINATION AND DEFECATION IN SPACE

CROSS-REFERENCE TO RELATED APPLICATIONS

This application is a Non-provisional application under 35 USC 111(a), which claims priority of Chinese Patent Application No. 201811331134.6, filed Nov. 9, 2018, the disclosure of which is hereby incorporated by reference in its entirety.

TECHNICAL FIELD

The application belongs to the field of aerospace technology, and in particular relates to a method of urination and defecation in space.

BACKGROUND OF THE INVENTION

At present, astronauts sail in space through spaceships. Due to the special environment in spaceships, there are always difficulties with the astronauts in urination and defecation, which has not been well solved up to now.

When astronauts perform tasks in space, they usually wear space diapers for urination and defecation, which causes pain to the astronauts because of excrements adhered to the body thereof. NASA said that if the excrements adhered to the body of astronauts for several days and could not be removed in time, dangerous infections would easily occur to the astronauts.

In the space station, the astronauts may use a space pumping toilet for urination and defecation, with which the excrements can be pumped away by gas stream, and the astronauts are fastened on a toilet seat of the space pumping toilet with his body, during which no excrements should escape.

There are disadvantages with the prior art that the space diaper cannot be worn for a long time, and leakage is likely to occur, causing damage to the astronaut's respiratory system. The cost of space toilets is high, needing 19 million US dollars in the United States, or 18 million RMB in China. Although there are high-end space toilets, this does not mean that it is easy to go to the toilet in space because it requires exact matching in seams, long time for preparation, operations with high difficulty and high precision, and it is difficult to absolutely prevent leakage and guarantee safety.

SUMMARY OF THE INVENTION

In view of the above problems in the prior art, the present disclosure provides a method of urination and defecation in space to facilitate astronauts working in space.

The above objects are achieved by the following technical solutions.

A method of urination and defecation in space is provided, may comprise forming a sealed space between a spacesuit below waist and above two thighs and human skin before an astronaut urinates or defecates; and using, by the astronaut, the sealed space to urinate or defecate.

In some embodiments, the forming a sealed space between a spacesuit below the waist and above the two thighs and the human skin may comprise: binding straps around the astronaut's waist and two thighs, so that the sealed space is formed between the spacesuit below the waist and above the two thighs and the human skin.

In some embodiments, a circle of elastic sealing tape is provided on an inner side of the spacesuit adjacent to the skin corresponding to the strap, so as to obtain a better sealing effect between a binding position of the spacesuit and the skin while tightening the straps.

In some embodiments, the forming a sealed space between a spacesuit below the waist and above the two thighs and the human skin may comprise: wearing, by the astronaut, a urination and defecation suit inside the spacesuit, and wherein the urination and defecation suit is worn on the skin of the astronaut from his waist to his two thighs, and the sealed space is formed between the urination and defecation suit and the human skin.

In some embodiments, the using, by the astronaut, the sealed space to urinate or defecate may comprise: providing a gas pumping mechanism as well as a spraying and flushing mechanism inside the sealed space, and providing a suction device and a sealed device outside the sealed space, wherein an input end of the suction device is connected to the sealed space through a first pipe, and an output end of the suction device is connected to the sealed device through a second pipe; during the astronaut's urination or defecation, the gas pumping mechanism and the suction device work to suck excrements into the sealed device; after the astronaut's urination or defecation, the gas pumping mechanism and the spraying and flushing mechanism work to flush the excrements adhered to the inner side of the spacesuit and the skin in the sealed space, and then the suction device continues to work to suck the flushed excrements into the sealed device.

In some embodiments, the first pipe is provided with a first reflux valve.

In some embodiments, the second pipe is provided with a second reflux valve.

In some embodiments, the sealed device is a sealed bag, and the sealed bag is suitable to be hung on the spacesuit.

In some embodiments, the sealed device is a sealed box, said sealed box being disposed in a spaceship or in a space station.

The beneficial effects of the disclosure are that: with the method of urination and defecation in space of the disclosure, a sealed space is formed between a spacesuit below the waist and above the two thighs and the human skin before an astronaut urinates or defecates, and the astronauts use the sealed space to urinate or defecate. Such a way of toileting can confine the excrements in a small sealed space, and the operation thereof is simple, convenient and fast, and no excessive cost is required, and no pollution is caused in the spacesuit and the cabin, facilitating the astronauts' work in space.

BRIEF DESCRIPTION OF THE DRAWINGS

In order to more clearly illustrate the technical solutions in the embodiments of the present disclosure, the drawings used in the description of the embodiments will be briefly described below. It is obvious that the drawings in the following description represent only some embodiments of the present disclosure. Other embodiments may also be obtained by those of ordinary skill in the art in light of these drawings without creative work.

DETAILED DESCRIPTION OF THE INVENTION

The technical solutions in the embodiments of the present disclosure will be clearly and fully described in the following with reference to the accompanying drawings in the embodiments of the present disclosure. It is obvious that the described embodiments are only a part of the embodiments of the present disclosure, but not all embodiments. All other embodiments obtained by those skilled in the art based on the embodiments of the present disclosure without creative efforts are within the scope of the present disclosure.

Figure 1:
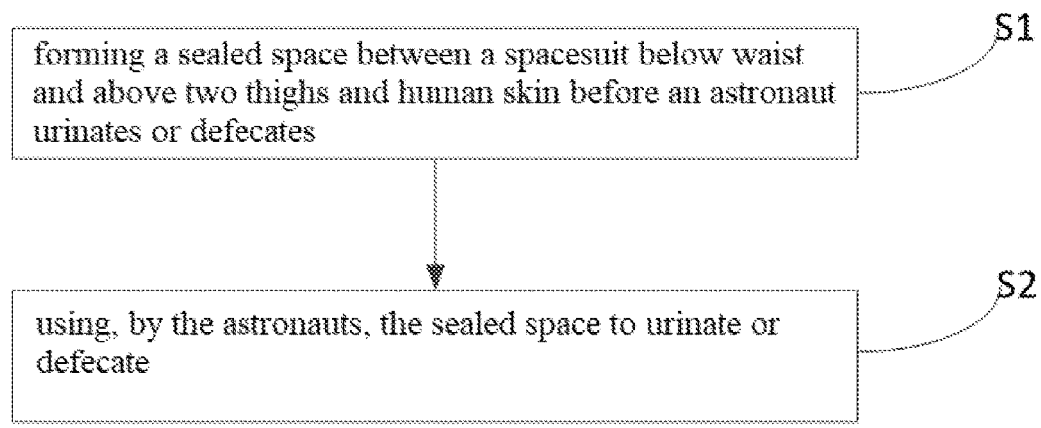
FIG. 1 is a schematic diagram of steps of a method of urination and defecation in space according to an embodiment of the present disclosure.

FIG. 1 is a schematic diagram of steps of a method of urination and defecation in space according to an embodiment of the present disclosure. Referring to FIG. 1, the method may comprise:

S1: forming a sealed space between a spacesuit below waist and above two thighs and human skin before an astronaut urinates or defecates; and S2: using, by the astronaut, the sealed space to urinate or defecate.

With the method of urination and defecation in space of the disclosure, the sealed space can be formed between the spacesuit below the waist and above the two thighs and the human skin before the astronaut urinates or defecates, and the astronauts use the sealed space to urinate or defecate. Such a way of toileting can confine the excrements in a small sealed space, and an operation thereof is simple, convenient and fast. Further, no excessive cost is required, and no pollution is caused in the spacesuit and the cabin, thereby facilitating the astronauts' work in space.

In some embodiments, a solution of forming a sealed space between a spacesuit below the waist and above the two thighs and the human skin may further comprise:

binding straps around the astronaut's waist and two thighs, so that the sealed space is formed between the spacesuit below the waist and above the two thighs and the human skin.

In the solution, the binding of the straps can be made manually or automatically by specialized machines, such as automatic binding machines common in the market, if only realizing fast binding and loosing of the straps, being convenient and fast.

Further, in some embodiments of the disclosure, a circle of elastic sealing tape is provided on an inner side of the spacesuit adjacent to the skin corresponding to the strap. The elastic sealing straps have proper widths and thicknesses and are soft, so as to facilitate tightening of the straps to obtain a better sealing effect between a binding position of the spacesuit and the skin.

In some embodiments, another solution of forming a sealed space between a spacesuit below the waist and above the two thighs and the human skin may comprise:

the astronaut may wear a urination and defecation suit inside the spacesuit, the urination and defecation suit being worn on the skin of the astronaut from his waist to his two thighs, so that the sealed space may be formed between the urination and defecation suit and the human skin. That is, the sealed space is realized by wearing a pre-fabricated half-set spacesuit. This way is much simpler and more convenient and can be used in a space station to replace a space toilet.

In some embodiments of the disclosure, a lining of the urination and defecation suit in the spacesuit, which is close to the skin, may be made of soft and waterproof material to facilitate good sealing in subsequent use and meet requirements of safety and sanitation.

In some embodiments, the step S2 may comprise the following.

Figure 2:
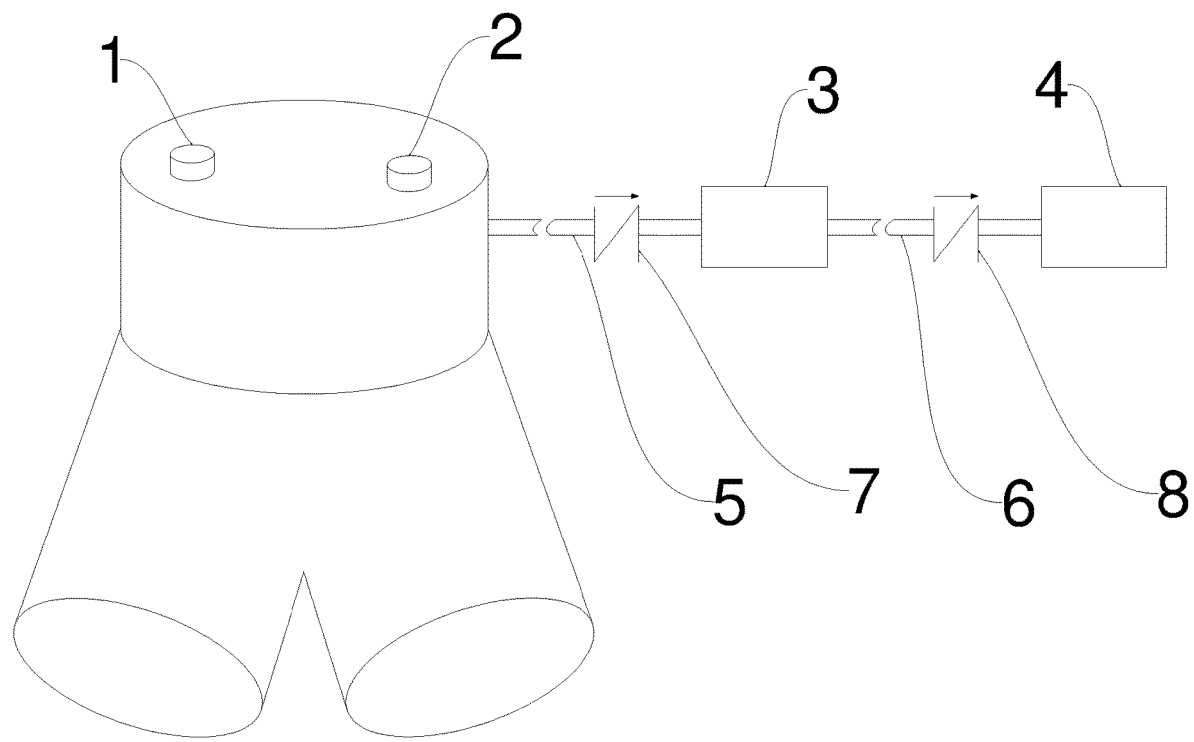
FIG. 2 is a schematic diagram showing structural arrangement within a sealed space.

FIG. 2 is a schematic diagram showing structural arrangement within the sealed space. Referring to FIG. 2, the sealed space may be provided with a gas pumping mechanism 1 and a spraying and flushing mechanism 2 therein. A suction device 3 and a sealed device 4 may be disposed outside the sealed space. An input end of the suction device 3 may be connected to the sealed space through a first pipe 5, and an output end of the suction device 3 may be connected to the sealed device 4 through a second pipe 6. During the astronaut's urination or defecation, the gas pumping mechanism 1 and the suction device 3 work to suck excrements into the sealed device 4. After the astronaut's urination or defecation, the gas pumping mechanism 1 and the spraying and flushing mechanism 2 work to flush the excrements adhered to the inner side of the spacesuit and the skin in the sealed space, and then the suction device 3 continues to work to suck the flushed excrements into the sealed device 4.

With the step S2 of the disclosure, the sealed space containing the excrements can be cleaned, and after cleaning, the sealed space can be released to facilitate the work of the astronaut.

Pumping gas to the sealed space during astronauts' urination or defecation has two functions: firstly, there must be sufficient pressure in the sealed space to prevent the clothes from sticking to the skin, so that the sealed space has a clear passage; secondly, the gas flow facilitates the excrements to be flushed toward the suction device 3 to be collected efficiently.

In some embodiments of the disclosure, the gas pumping mechanism 1 and the spraying and flushing mechanism 2 may be directly installed in the sealed space of the spacesuit, and the dirt adhered to the skin and the clothes can be washed away by adding water and pumping gas. The suction device 3 can be hung on a spacesuit or at a suitable place in a spaceship or space station to facilitate the astronauts to pick up.

Further, in some embodiments of the disclosure, the first pipe 5 may be provided with a first reflux valve 7, and the second pipe 6 may be provided with a second reflux valve 8, so that the excrements can be prevented from flowing back to the sealed space from the sealed device 4.

Further, the sealed device 4 of an embodiment is convenient to be cleaned and purified for use subsequently, which can be a sealed bag, and the sealed bag is suitable to be hung on a spacesuit to facilitate the astronauts' work outside the spaceship.

Of course, the sealed device 4 of an embodiment of the disclosure may be a sealed box, and the sealed box may be disposed in a spaceship or in a space station to facilitate the astronauts' work in the spaceship or space station.

Since the excrements can be collected by the sealed device 4 in the embodiments of the disclosure, it is possible to prevent pollutions in the spacesuit and the cabin caused by the excrements, thereby improving cleanness.

It should be noted that, in the embodiments of the present disclosure, after the astronauts' urination or defecation and the excrements are cleaned, the binding straps can be loosened. Alternatively, the binding straps and the binding machine can be worn in order to be used at any time when needed.

The embodiments of the present disclosure can be adapted commonly to male astronauts and female astronauts, and the astronaut's fart or menstrual blood can also be collected in the same manner.

The above embodiments are only preferred embodiments of the disclosure and intended to illustrate the invention conveniently rather than limiting the invention in any form. Any equivalent embodiments with partial modifications or verifications made by those of ordinary skill in the art within the scope of the technical features of the present invention in the light of the technical content disclosed in the present invention, without departing from the technical features of the present invention, are all within the scope of invention.

The invention claimed is:

1. A method of waste collection in space, comprising:
    binding straps around an astronaut's waist and two thighs to form a sealed space between a spacesuit and a skin of the astronaut, below the astronaut's waist and above the astronaut's two thighs, before the astronaut urinates or defecates;
    pressurizing the sealed space to thereby provide a clear passage in the sealed space, wherein said pressurizing also provide an air flow; flushing excrements in the sealed space with the air flow provided by said pressurizing; and
    automatically loosening the straps after the astronauts' urination or defecation in the sealed space and upon completion of said flushing;
    wherein a circle of elastic sealing tape is provided on an inner side of the spacesuit adjacent to a skin area corresponding to one of the straps to obtain a sealing effect between a binding position of the spacesuit and the skin, and the elastic sealing tape is soft.

2. The method according to claim 1, further comprising:
    providing a gas pumping mechanism as well as a spraying and flushing mechanism inside the sealed space, and providing a suction device and a sealed device outside the sealed space, wherein an input end of the suction device is connected to the sealed space through a first pipe, and an output end of the suction device is connected to the sealed device through a second pipe;
    during the astronaut's urination or defecation, the gas pumping mechanism and the suction device functioning to suck the excrements into the sealed device; and
    after the astronaut's urination or defecation, the gas pumping mechanism and the spraying and flushing mechanism providing the air flow to flush the excrements adhered to an inner side of the spacesuit and the skin in the sealed space, and then the suction device continuing suction of the flushed excrements into the sealed device,
    wherein the gas pumping mechanism provides said pressurizing the sealed space to prevent the spacesuit from sticking to the skin, and the air flow facilitates the excrements to be flushed toward the suction device.

3. The method according to claim 2, wherein the first pipe is provided with a first reflux valve.

4. The method according to claim 2, wherein the second pipe is provided with a second reflux valve.

5. The method according to claim 2, wherein the sealed device is a sealed bag, and the sealed bag is suitable to be hung on the spacesuit.

6. The method according to claim 2, wherein the sealed device is a sealed box, said sealed box being disposed in a spaceship or in a space station.

* * * * *